(12) United States Patent
Han et al.

(10) Patent No.: US 10,821,065 B2
(45) Date of Patent: Nov. 3, 2020

(54) PEPTIDE FOR INHIBITING BIOFILMS

(71) Applicants: SEOUL NATIONAL UNIVERSITY R&DB FOUNDATION, Seoul (KR); NIBEC CO., LTD., Chungcheongbuk-do (KR)

(72) Inventors: Seung Hyun Han, Seoul (KR); Kee-Yeon Kum, Seoul (KR); Ki Bum Ahn, Gyeonggi-do (KR); Ok-Jin Park, Seoul (KR); Chong-Pyoung Chung, Seoul (KR); Yoon Jeong Park, Seoul (KR); Jue-Yeon Lee, Gyeonggi-do (KR)

(73) Assignees: SEOUL NATIONAL UNIVERSITY R&DB FOUNDATION, Seoul (KR); NIBEC CO., LTD., Chungcheongbuk-Do (KR)

( * ) Notice: Subject to any disclaimer, the term of this patent is extended or adjusted under 35 U.S.C. 154(b) by 0 days.

(21) Appl. No.: 16/498,951

(22) PCT Filed: Mar. 19, 2018

(86) PCT No.: PCT/KR2018/003162
§ 371 (c)(1),
(2) Date: Sep. 27, 2019

(87) PCT Pub. No.: WO2018/186607
PCT Pub. Date: Oct. 11, 2018

(65) Prior Publication Data
US 2020/0113801 A1   Apr. 16, 2020

(30) Foreign Application Priority Data

Apr. 5, 2017 (KR) .................. 10-2017-0044233

(51) Int. Cl.
A61K 8/64 (2006.01)
A61K 8/19 (2006.01)
A61K 8/43 (2006.01)
A61Q 11/00 (2006.01)

(52) U.S. Cl.
CPC .............. *A61K 8/64* (2013.01); *A61K 8/19* (2013.01); *A61K 8/43* (2013.01); *A61Q 11/00* (2013.01)

(58) Field of Classification Search
None
See application file for complete search history.

(56) References Cited

U.S. PATENT DOCUMENTS

2008/0274095 A1   11/2008   Homan et al.

FOREIGN PATENT DOCUMENTS

KR   1020110098685 A   9/2011
KR      101257228 B    4/2013

OTHER PUBLICATIONS

Lee et al. "Antibacterial Efficacy of a Human beta-Defensin-3 Peptide on Multispecies Biofilms," Journal of Endontics, vol. 39, No. 12, 2013, pp. 1625-1629 (Year: 2013).*
Lee et al. "Antimicrobial efficacy of a human beta-defensin-3 peptide using an Enterococcus faecalis dentine infection model," International Endodontic Journal, 46, 406-412, 2013 (Year: 2013).*
Kishen et al. "Enterococcus faecalis-mediated biomineralized biofilm formation on root canal dentine in vitro," J Biomed Mater Res A. May 2006;77(2):406-15 (Year: 2006).*
Virtual Museum of Molecules and Minerals "Portlandite" dowloaded Mar. 18, 2020 (Year: 2020).*
Arabaci, T., et al., "Assessment of Cytogenetic and Cytotoxic Effects of Chlorhexidine Digluconate on Cultured Human Lymphocytes", "Acta Odontologica Scandinavica", 2013, pp. 1255-1260, vol. 71.
Bramante, C., et al., "Alveolar Mucosa Necrosis Induced by Utilisation of Calcium Hydroxide as Root Canal Dressing", "International Dental Journal", 2008, pp. 81-85, vol. 58.
Lim, S., et al., "Antifungal Effects of Synthetic Human Beta-Defensin 3-C15 Peptide", "Restorative Dentistry & Endodontics", 2016, pp. 91-97, vol. 41, No. 2.
Pepperney, A., et al., "Antibacterial Peptides: Opportunities for the Prevention and Treatment of Dental Caries", "Probiotics & Antimicro. Prot.", 2011, pp. 68-96, vol. 3.
Slot, D.E., et al., "The Efficacy of Chlorhexidine Dentifrice or Gel on Plaque, Clinical Parameters of Gingival Inflammation and Tooth Discoloration: A Systematic Review", "International Journal of Dental Hygiene", 2014, pp. 25-35, vol. 12.
Supranoto, S.C., et al., "The Effect of Chlorhexidine Dentifrice or Gel Versus Chlorhexidine Mouthwash on Plaque, Gingivitis, Bleeding and Tooth Discoloration: A Systematic Review", "International Journal of Dental Hygiene", 2015, pp. 83-92, vol. 13.
Yoo, Y., et al., "Antifungal Effects of Synthetic Human Beta-Defensin-3-C15 Peptide on Candida Albicans-Infected Root Dentin", "Journal of Endodontics", Nov. 2017, pp. 1857-1861, vol. 43, No. 11.

* cited by examiner

*Primary Examiner* — Christina Bradley
(74) *Attorney, Agent, or Firm* — Hultquist, PLLC; Steven J. Hultquist

(57) ABSTRACT

The present invention relates to: a composition for inhibiting biofilms, containing, as an active ingredient, a peptide derived from human β-defensin-3; and a method for inhibiting biofilms by using the composition. The peptide according to the present invention inhibits bacterial biofilms even when used alone and exhibits a remarkably increased biofilm inhibitory effect when used in combination with a conventional dental therapeutic agent, and has an effect of preventing a tooth discoloration side effect caused by a conventional dental therapeutic agent.

11 Claims, 3 Drawing Sheets
(3 of 3 Drawing Sheet(s) Filed in Color)
Specification includes a Sequence Listing.

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Peptide fragment derived from Human beta-
      defensin-3

<400> SEQUENCE: 1

Gly Lys Cys Ser Thr Arg Gly Arg Lys Cys Cys Arg Arg Lys Lys
1               5                   10                  15
```

PEPTIDE FOR INHIBITING BIOFILMS

CROSS-REFERENCE TO RELATED APPLICATIONS

This application is a U.S. national phase under the provisions of 35 U.S.C. § 371 of International Patent Application No. PCT/KR18/03162 filed Mar. 19, 2018, which in turn claims priority of Korean Patent Application No. 10-2017-0044233 filed Apr. 5, 2017. The disclosures of International Patent Application No. PCT/KR18/03162 and Korean Patent Application No. 10-2017-0044233 are hereby incorporated herein by reference in their respective entireties, for all purposes.

TECHNICAL FIELD

The present invention relates to a peptide for inhibiting a biofilm, and more particularly to a composition for inhibiting a biofilm which comprises, as an active ingredient, a peptide derived from human beta-defensin-3, and a method of inhibiting a biofilm using the composition.

BACKGROUND ART

Dental infectious diseases such as dental caries, apical periodontitis, and periodontitis are caused by bacterial infection. These are known as diseases accompanied by inflammation, bleeding, loose teeth, and loss of teeth. Representative bacteria causing such dental infectious diseases include *Streptococcus mutans, Enterococcus faecalis, Streptococcus gordonii*, and the like.

As mentioned above, the onset of these dental infectious diseases is caused by bacterial infection, but the biofilm formation of bacteria directly affects the progress and severity of dental infectious diseases. Generally, bacteria are rarely suspended and dispersed alone, and most of them are colonized by being attached to teeth, human tissues, and medical prostheses by polymers produced by bacteria themselves. Such a complex formed by bacteria is called a biofilm.

Bacteria that proliferate on a biofilm are about 10 to about 1,000 times more resistant to antibiotics than those in a suspended form. Generally, even when antibiotics known to have an antimicrobial effect on suspended bacteria are used, it is often impossible to inhibit biofilms by using the antibiotics. Accordingly, antibiotics are used in excessive doses, and antibiotic-resistant strains are proliferating due to the abuse of antibiotics. In addition, biofilms are not effectively removed by conventionally known dental therapeutic agents, and thus induce secondary infections by remaining bacteria and cause recurrent diseases such as intractable apical periodontitis.

Dental therapeutic agents, which are currently used clinically for dental infectious diseases, have been reported to have various side effects. Representative dental therapeutic agents include calcium hydroxide, chlorohexidine, triple complex antibiotics, and the like, and side effects include tissue necrosis, sensory abnormalities, tooth discoloration, allergic reactions, and the like (Int J Dent Hygiene 12, 2014; 25-35, Int J Dent Hygiene 13, 2015; 83-92, Acta Odontologica Scandinavica, 2013; 71: 1255-1260, International Dental Journal, 2008; 58: 81-85).

As such, increasing the dose of a dental therapeutic agent for the removal of a biofilm has limitations due to side effects on the human body. Therefore, there is a need to develop a bio-friendly new dental therapeutic agent capable of efficiently controlling a biofilm without side effects.

Human beta-defensin-3 is one of human-derived antibiotics, which is widely expressed in the oral cavity, the respiratory organs, and the digestive organs, and is known to have an antibiotic effect on various bacteria. It is known that positively charged amino acids play an important role in the antibiotic effect of human beta-defensin-3 and a large amount of positively charged amino acids are present at the C-terminus of human beta-defensin-3.

Therefore, the inventors of the present invention synthesized 15 amino acids from the C-terminus, at which a large amount of positively charged amino acids of human beta-defensin-3 are present, confirmed that the peptide alone not only inhibited oral bacterial biofilms, but also more effectively inhibited biofilms through a synergistic effect with existing dental therapeutic agents, and verified the efficacy thereof, thus completing the present invention.

DISCLOSURE

Technical Problem

Therefore, the present invention has been made in view of the above problems, and it is an object of the present invention to provide a composition for inhibiting a biofilm, which comprises, as an active ingredient, a peptide derived from human beta-defensin-3.

It is another object of the present invention to provide a method of inhibiting a biofilm using the composition.

It is a further object of the present invention to provide a composition for preventing tooth discoloration, which comprises, as an active ingredient, a peptide derived from human beta-defensin-3.

Technical Solution

In accordance with the present invention, the above and other objects can be accomplished by the provision of a composition for inhibiting a biofilm, the composition comprising, as an active ingredient, a peptide set forth in an amino acid sequence of SEQ ID NO: 1.

In accordance with another aspect of the present invention, there is provided a method of inhibiting a biofilm, the method comprising treating a surface with a biofilm formed thereon or on which biofilm formation is expected, with the composition.

In accordance with another aspect of the present invention, there is provided a composition for preventing tooth discoloration, the composition comprising, as an active ingredient, a peptide set forth in an amino acid sequence of SEQ ID NO: 1.

In accordance with another aspect of the present invention, there is provided a method of preventing tooth discoloration, the method comprising treating a tooth with the composition.

In accordance with another aspect of the present invention, there is provided a use of a peptide set forth in an amino acid sequence of SEQ ID NO: 1 for inhibiting a biofilm.

In accordance with another aspect of the present invention, there is provided a use of a peptide set forth in an amino acid sequence of SEQ ID NO: 1 for preventing tooth discoloration.

DESCRIPTION OF DRAWINGS

The patent or application file contains at least one drawing executed in color. Copies of this patent or patent application

BEST MODE

Figure 1:
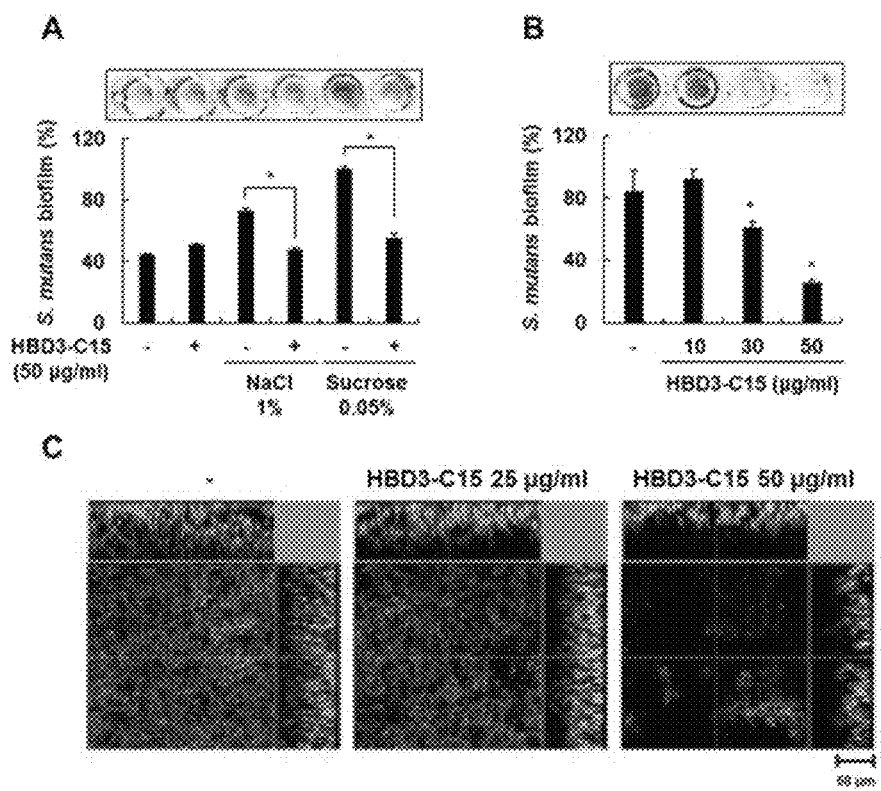
FIG. 1 illustrates the results of confirming the effect of a peptide set forth in an amino acid sequence of SEQ ID NO: 1 on inhibiting a biofilm formed by *Streptococcus mutans*.

Hereinafter, the present invention will be described in detail. The terms or words used in the present specification and claims should not be construed as being limited to ordinary or dictionary meanings but should be construed as having meanings and concepts consistent with the spirit of the present invention based on the principle that an inventor can appropriately define the concepts of terms to explain the invention of the inventor in the best way. Thus, the configurations described in the embodiments set forth herein are merely exemplary embodiments of the present invention and do not represent all technical ideas of the present invention, and thus it should be understood that various equivalents and modifications that may replace these embodiments can be made at the time of filing of the present application.

The inventors of the present invention confirmed that a peptide alone consisting of 15 amino acids at the C-terminus where a large quantity of positively charged amino acids are present not only inhibited an oral bacterial biofilm, but also significantly enhanced a biofilm inhibitory effect when used in combination with an existing dental therapeutic agent, and was able to prevent side effects such as tooth discoloration caused by existing dental therapeutic agents, and thus completed the present invention.

Therefore, an embodiment of the present invention relates to a composition for inhibiting a biofilm, which comprises, as an active ingredient, a peptide set forth in an amino acid sequence of SEQ ID NO: 1.

The peptide of the present invention is used in any case where biofilms are formed by a microorganism without limitation, and may act on the surface of a living or non-living organism on which a microorganism is able to form a biofilm. Examples of the surface thereof may include living-organism-derived tissues or organs, metal surfaces, oral hygiene products such as toothbrushes, dental floss, interdental brushes, tongue cleaners, oral tissues, and the like, dental products such as ceramic surfaces and the like, kitchen appliances, bath supplies, and areas that are continuously in contact with water such as water and sewage pipes, washing machines, laundry tanks, and the like. Preferably, the surface may be the oral mucosa, a tooth surface, a toothbrush surface, or a surface of a glass plate which is frequently in contact with water.

The peptide may be included in the composition according to the present invention at a concentration of 1 µg/ml to 1,000 µg/ml, preferably 10 µg/ml to 100 µg/ml. When the concentration of the peptide is less than 1 µg/ml, the biofilm inhibitory effect is insignificant.

The composition according to the present invention is not limited to use for the inhibition of a biofilm formed by a specific microorganism, but particularly may be used for the inhibition of a biofilm formed by infectious bacteria selected from the group consisting of *Streptococcus mutans, Enterococcus faecalis, Streptococcus gordonii, Lactobacillus salivarius*, and *Actinomyces naeslundii*.

The use of the composition of the present invention is not limited, but particularly, the composition of the present invention may be used as an oral composition. More specifically, the oral composition according to the present invention is capable of inhibiting the formation of a biofilm formed by *Streptococcus mutans*, which is the main cause of plaques, and thus may be used for maintaining and improving oral health, such as for the inhibition of dental caries, the prevention of stomatitis, and the like. When the composition according to the present invention is used for the oral cavity, the composition may further include ingredients that are commonly used in the preparation of an oral composition, such as a wetting agent, an abrasive, a medicinal agent, a sweetener, a preservative, a binder, a flavoring agent, a foaming agent, water, or the like.

The composition of the present invention may further include calcium hydroxide or chlorohexidine. When the composition is used in combination with calcium hydroxide or chlorohexidine, tooth discoloration, which is one of side effects caused by calcium hydroxide or chlorohexidine, is prevented, and the biofilm inhibitory effect is significantly enhanced.

Another embodiment of the present invention relates to a method of inhibiting a biofilm, comprising treating a surface with a biofilm formed thereon or on which the formation of a biofilm is expected, with a composition comprising, as an active ingredient, a peptide set forth in an amino acid sequence of SEQ ID NO: 1.

The surface with a biofilm formed thereon or on which biofilm formation is expected may be a surface of a living or non-living organism, and the biofilm may be formed by infectious bacteria selected from the group consisting of *Streptococcus mutans, Enterococcus faecalis, Streptococcus gordonii, Lactobacillus salivarius*, and *Actinomyces naeslundii*, but the present invention is not limited thereto.

Another embodiment of the present invention relates to a method of inhibiting a biofilm, comprising treating a surface with a biofilm formed thereon or on which biofilm formation is expected, with a composition comprising a peptide set forth in an amino acid sequence of SEQ ID NO: 1 as an active ingredient, and further comprising calcium hydroxide or chlorohexidine as an additional active ingredient.

The biofilm according to the present invention may be a biofilm formed on a tooth surface, and the method according to the present invention is characterized by the prevention of tooth discoloration caused by calcium hydroxide or chlorohexidine.

Another embodiment of the present invention relates to a composition for preventing tooth discoloration, which comprises, as an active ingredient, a peptide set forth in an amino acid sequence of SEQ ID NO: 1.

The composition according to the present invention may inhibit tooth discoloration caused by a dental therapeutic agent, and the dental therapeutic agent may be calcium hydroxide or chlorohexidine, but the present invention is not limited thereto.

Another embodiment of the present invention relates to a method of preventing tooth discoloration, comprising treating a tooth with the composition.

Another embodiment of the present invention relates to a use of a peptide set forth in an amino acid sequence of SEQ ID NO: 1 for inhibiting a biofilm.

Another embodiment of the present invention relates to a use of a peptide set forth in an amino acid sequence of SEQ ID NO: 1 for preventing tooth discoloration.

EXAMPLES

Hereinafter, the present invention will be described in more detail with reference to the following examples. These examples are provided for illustrative purposes only, and it will be obvious to those of ordinary skill in the art that these examples should not be construed as limiting the scope of the present invention.

The peptide used in the present invention is a peptide fragment (HBD3-C15) derived from human beta-defensin-3 (HBD3). The sequence of the peptide is as follows.

HBD3-C15 (SEQ ID NO: 1): G-K-C-S-T-R-G-R-K-C-C-R-R-K-K

Example 1

Effect of HBD3-C15 on *Streptococcus mutans* Biofilm Formation

To confirm the effect of HBD3-C15 on a *Streptococcus mutans* biofilm, *Streptococcus mutans* was cultured in a Brain Heart Infusion (BHI) medium. The cultured *Streptococcus mutans* was prepared at $1\times10^7$ CFU/ml, and then 1% NaCl or 0.05% sucrose was added thereto to promote biofilm formation, followed by treatment with 50 µg/ml of HBD3-C15. After incubation at 37° C. for 24 hours, 0.1% crystal violet staining was performed for comparison of the degree of biofilm formation. The experimental results showed that, as illustrated in FIG. 1A, HBD3-C15 inhibited the formation of a *Streptococcus mutans* biofilm formed by NaCl or sucrose (see FIG. 1A).

In addition, 0.05% sucrose was added to *Streptococcus mutans*, followed with treatment with HBD3-C15 at a concentration of 10 µg/ml, 30 µg/ml, or 50 µg/ml. After incubation at 37° C. for 24 hours, 0.1% crystal violet staining was performed for comparison of the degree of biofilm formation. The experimental results showed that the formation of a *Streptococcus mutans* biofilm was inhibited in a concentration-dependent manner (see FIG. 1B). This tendency for HBD3-C15 to inhibit formation of a biofilm in a concentration-dependent manner was also confirmed using a confocal microscope (see FIG. 1C).

Example 2

Figure 2:
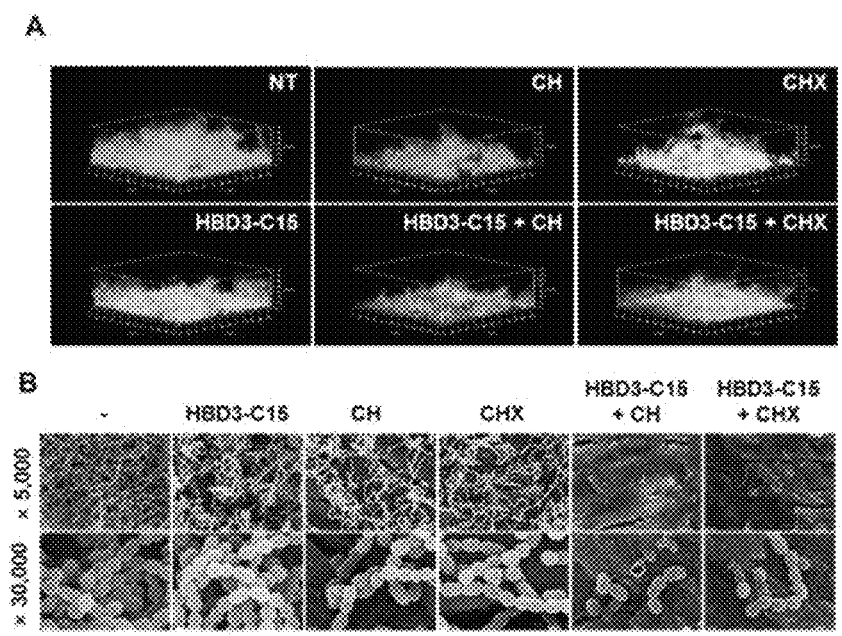
FIG. 2 illustrates the results of confirming the effect of single treatment with a peptide set forth in an amino acid sequence of SEQ ID NO: 1 or co-treatment with the peptide and calcium hydroxide or chlorohexidine on inhibiting a biofilm formed by *Streptococcus mutans*.

Effect of Treatment with HBD3-C15 or Co-Treatment with HBD3-C15 and Calcium Hydroxide (CH) or Chlorohexidine (CHX) on *Streptococcus mutans* Biofilm Formation To determine whether HBD3-C15 is capable of inhibiting a biofilm by synergistic effects with calcium hydroxide (CH) or chlorohexidine (CHX), which is an existing dental therapeutic agent, *Streptococcus mutans* was cultured in a BHI medium and then prepared at $1\times10^7$ CFU/ml, and treated with 10 µg/ml of HBD3-C15, 25 µg/ml of CH, 0.02% CHX, or a combination thereof in the presence of 0.05% sucrose. After incubation at 37° C. for 24 hours, 0.1% crystal violet staining was performed for comparison of the degree of biofilm formation. The experimental results showed that, while the *S. mutans* biofilm formation was inhibited when treated with HBD3-C15, CH, or CHX alone, the biofilm formation was more strongly inhibited by synergistic effects upon co-treatment thereof, with, for example, HBD3-C15+CH and HBD3-C15+CHX (see FIG. 2A).

In addition, human teeth dentin sections were prepared to represent an actual oral infection situation, $1\times10^7$ CFU/ml of *Streptococcus mutans* was treated, on the dentin sections, with 10 µg/ml of HBD3-C15, 25 µg/ml of CH, 0.02% CHX, or a combination thereof in the presence of 0.05% sucrose. After incubation at 37° C. for 24 hours, comparison of the degree of biofilm formation was conducted using a scanning electron microscope. It was confirmed from the experimental results that, as in the results of FIG. 2A, the *S. mutans* biofilm formation was inhibited when treated with HBD3-C15, CH, or CHX alone, while biofilm formation was more strongly inhibited by synergistic effects upon co-treatment with, for example, HBD3-C15+CH or HBD3-C15+CHX (see FIG. 2B).

Example 3

Figure 3:
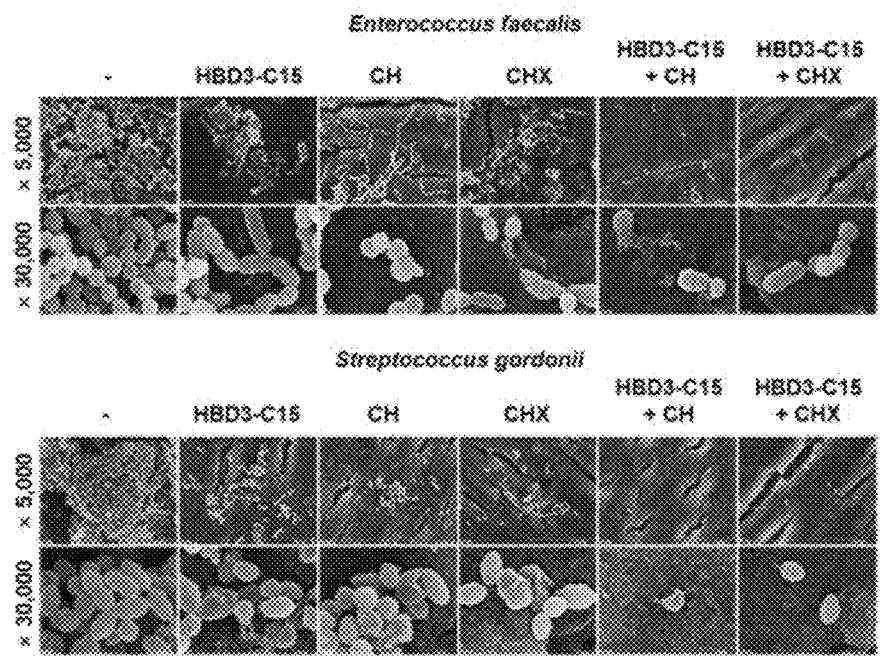
FIG. 3 illustrates the results of confirming the effect of single treatment with a peptide set forth in an amino acid sequence of SEQ ID NO: 1 or co-treatment with the peptide and calcium hydroxide or chlorohexidine on inhibiting a biofilm formed by *Enterococcus faecalis* or *Streptococcus gordonii*.

Effect of Treatment with HBD3-C15 or Co-Treatment with HBD3-C15 and Calcium Hydroxide or Chlorohexidine on Biofilms Formed by Various Oral Infectious Bacteria To confirm whether the *Streptococcus mutans* biofilm inhibition through synergistic effects of HBD3-C15 and an existing dental therapeutic agent is reproduced in the formation of biofilms formed by other dental infectious bacteria, *Enterococcus faecalis* and *Streptococcus gordonii* were cultured in a BHI medium and a Todd Hewitt yeast (THY) medium, respectively, and then *E. faecalis* and *S. gordonii* were prepared at $5\times10^6$ CFU/ml and $1\times10^8$ CFU/ml, respectively, and treated, on the dentin sections, with 10 µg/ml of HBD3-C15, 25 µg/ml of CH, 0.02% CHX, or a combination thereof. After incubation at 37° C. for 24 hours, comparison of the degree of biofilm formation was conducted using a scanning electron microscope. The experimental results showed that, as in the results of FIG. 2B, the biofilm formation was inhibited when treated with HBD3-C15, CH, or CHX alone, while the formation of *E. faecalis* and *S. gordonii* biofilms was more strongly inhibited by synergistic effects upon co-treatment with, for example, HBD3-C15+CH or HBD3-C15+ CHX (see FIG. 3).

Example 4

Figure 4:
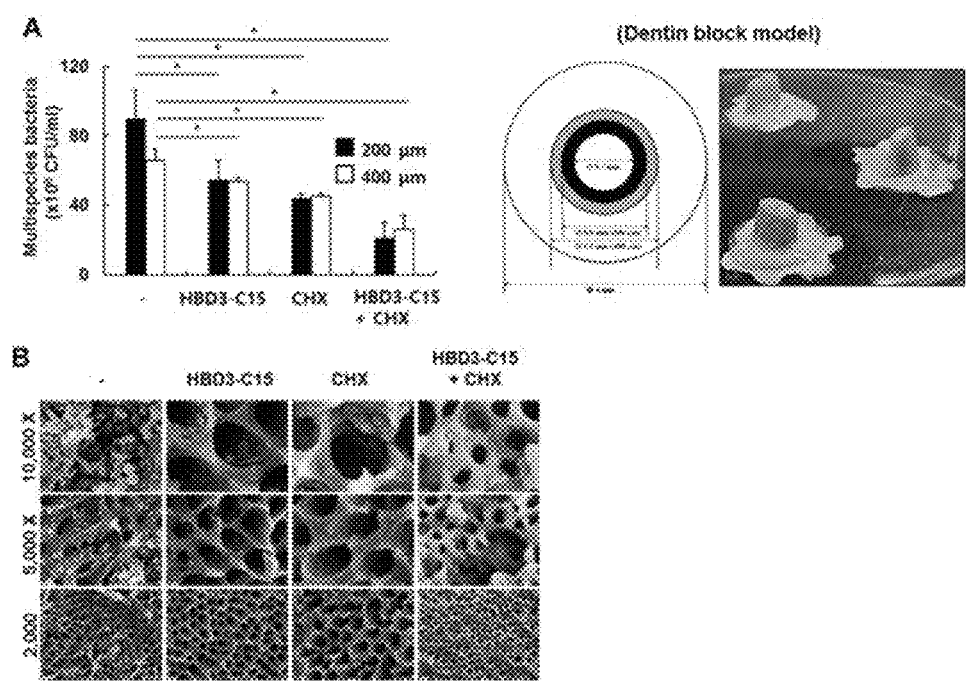
FIG. 4 illustrates the results of confirming the effect of single treatment with a peptide set forth in an amino acid sequence of SEQ ID NO: 1 or co-treatment with the peptide and chlorohexidine on inhibiting a biofilm on the surface of the dentinal tubules and in the dentinal tubules.
Figure 5:
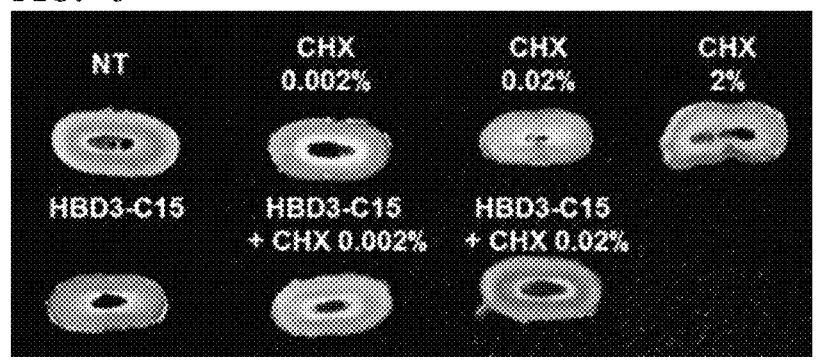
FIG. 5 illustrates the results of confirming the effect of single treatment with a peptide set forth in an amino acid sequence of SEQ ID NO: 1 or co-treatment with the peptide and chlorohexidine on color discoloration.

Effect of Treatment with HBD3-C15 Alone or Co-Treatment with HBD3-C15 and Chlorohexidine on Multispecies Bacteria To confirm whether the biofilm inhibitory effect through synergistic effects of HBD3-C15 and an existing dental therapeutic agent is also exhibited in biofilms on the surface of the dentinal tubules and in the dentinal tubules, a human teeth dentin block with a 0.7 mm root canal was constructed to represent an actual dentin tubular infection situation, and the root canal of the dentin block was treated with a mixture of the same amount of *Streptococcus mutans, Enterococcus faecalis, Lactobacillus salivarius*, and *Actinomyces naeslundii*, and cultured for 3 weeks to induce the formation of biofilms on the surface of the dentinal tubules and in the dentinal tubules. Subsequently, the root canal of the dentin block was treated with 30 μg/ml of HBD3-15, 0.2% CHX, or a combination thereof for 3 days, and then dental chips which contain 200 μm and 400 μm length dentinal tubules, were obtained from the inside of the root canal by using #90 and #110 LightSpeed Ni-Ti rotary files. Each dental chip was diluted in a BHI medium, and then cultured in a solid medium for 24 hours to count the number of colonies of bacteria infiltrated up to the depths of the dentinal tubules of 200 μm and 400 μm and the effect of treatment with HBD3-C15 or CHX alone or treatment with a combination thereof on inhibiting biofilms formed by bacteria were observed. From the experimental results, it was confirmed that biofilms formed by the bacteria that infiltrated into the depths of 200 μm and 400 μm were inhibited by distinct synergistic effects of co-treatment with HBD3-C15 and CHX (see FIG. 4A).

In addition, bacteria were cultured for 3 weeks and subjected to treatment with the drugs alone or a combination thereof in the same manner as described above, and then the degrees of biofilm formation on the surface of the dentinal tubules and in the dentinal tubules in the dentin block were observed using an SEM. The experimental results showed that biofilms present on the surface of the dentinal tubules and in the dentinal tubules were inhibited by treatment with HBD3-C15 or CHX alone. However, the biofilm formed by bacteria on the surface of the dentinal tubules was more strongly inhibited by co-treatment with HBD3-C15 and CHX than single treatment, and the biofilm formed in the dentinal tubules was also effectively controlled thereby (see FIG. 4B).

Example 5

Effect of Treatment with HBD3-C15, Chlorohexidine, or Combination thereof on Tooth Discoloration According to previous papers, it has been reported that CHX, which is a typical dental therapeutic agent, causes side effects such as tooth discoloration. Thus, to confirm the effect of treatment with HBD3-C15 alone or a combination of HBD3-C15 and CHX on tooth discoloration, dentin sections were treated with 30 μg/ml of HBD3-C15, 0.002% CHX, 0.02% CHX, or a combination thereof, and 2% CHX was used as a positive control. Subsequently, the dentin sections were cultured at 37° C. for 7 days and photographed to observe the degree of tooth discoloration.

The experimental results showed that tooth discoloration was induced by treatment with CHX alone in a concentration-dependent manner, and tooth discoloration was not induced by treatment with HBD3-C15 alone. In addition, the case of co-treatment with HBD3-C15 and CHX did not induce color discoloration. These results suggest that HBD3-C15 has a potential of reducing the concentration of an existing dental therapeutic agent used and minimizing side effects on the human body caused by existing dental therapeutic agents.

While particular embodiments of the present invention have been described in detail, it will be obvious to those of ordinary skill in the art that these detailed descriptions are exemplary embodiments only and are not intended to limit the scope of the present invention. Thus, the actual scope of the present invention is construed as being defined by the appended claims and equivalents thereto. Simple modifications and changes of the present invention can be readily used by those of ordinary skill in the art, and these modifications or changes should be construed as being within the scope of the present invention.

ABBREVIATION

CH: Calcium hydroxide
CHX: Chlorohexidine

INDUSTRIAL APPLICABILITY

As is apparent from the above description, a peptide of the present invention has an excellent effect of inhibiting a biofilm even when used alone, and when used in combination with an existing dental therapeutic agent having antimicrobial activity, the biofilm inhibitory effect is significantly enhanced. The peptide also has an effect of inhibiting side effects such as tooth discoloration and the like caused by conventional dental therapeutic agents, and thus can be used for dental applications. In addition, the peptide can be widely used in various industrial field as long as it is used for inhibiting the formation of a biofilm.

SEQUENCE LIST FREE TEXT

Electronic files attached.

The invention claimed is:

1. A method of preventing tooth discoloration caused by a dental therapeutic agent, the method comprising treating tooth with a composition comprising a peptide set forth in the amino acid sequence of SEQ ID NO: 1.

2. The method of claim 1, wherein the dental therapeutic agent is calcium hydroxide or chlorohexidine.

3. The method of claim 1, wherein the composition contains any of a wetting agent, an abrasive, a medicinal agent, a sweetener, a preservative, a binder, a flavoring agent, a foaming agent, and water.

4. The method of claim 1, wherein the composition contains calcium hydroxide or chlorohexidine.

5. The method of claim 4, wherein the peptide is in the composition at a concentration of 1 μg/ml to 30 μg/ml.

6. The method of claim 5, wherein the composition contains chlorohexidine.

7. The method of claim 5, wherein the composition contains calcium hydroxide.

8. A method of preventing tooth discoloration in treatment of a tooth with chlorhexidine or calcium hydroxide, the method comprising co-treating the tooth being treated with chlorhexidine or calcium hydroxide, with a composition comprising a peptide consisting of the amino acid sequence of SEQ ID NO: 1.

9. The method of claim 8, wherein the composition contains the peptide at a concentration of 1 μg/ml to 30 μg/ml.

10. The method of claim 9, wherein the tooth is treated with chlorhexidine.

11. The method of claim 9, wherein the tooth is treated with calcium hydroxide.

* * * * *

UNITED STATES PATENT AND TRADEMARK OFFICE
CERTIFICATE OF CORRECTION

PATENT NO. : 10,821,065 B2
APPLICATION NO. : 16/498951
DATED : November 3, 2020
INVENTOR(S) : Han et al.

Page 1 of 1

It is certified that error appears in the above-identified patent and that said Letters Patent is hereby corrected as shown below:

On the Title Page

Under OTHER PUBLICATIONS, Line 10, in the fourth citation:
"dowloaded Mar. 18, 2020"
Should be:
-- downloaded Mar. 18, 2020 --.

Signed and Sealed this
Eighth Day of December, 2020

Andrei Iancu
*Director of the United States Patent and Trademark Office*